(12) United States Patent
Mayer-Posner et al.

(10) Patent No.: US 6,414,306 B1
(45) Date of Patent: Jul. 2, 2002

(54) TLC/MALDI CARRIER PLATE AND METHOD FOR USING SAME

(75) Inventors: Franz-Josef Mayer-Posner, Lilienthal; Jochen Franzen, Bremen, both of (DE)

(73) Assignee: Bruker Daltonik GmbH, Bremen (DE)

( * ) Notice: Subject to any disclaimer, the term of this patent is extended or adjusted under 35 U.S.C. 154(b) by 0 days.

(21) Appl. No.: 09/632,448

(22) Filed: Aug. 4, 2000

(30) Foreign Application Priority Data

Aug. 7, 1999 (DE) .......................................... 199 37 438

(51) Int. Cl.[7] .......................... B01D 59/44; H01J 49/00
(52) U.S. Cl. ...................................... 250/288; 250/281
(58) Field of Search ................................ 250/288, 281; 436/173, 174

(56) References Cited

U.S. PATENT DOCUMENTS

| | | | |
|---|---|---|---|
| 3,896,661 A | * 7/1975 | Parkhurst et al. | 73/23.1 |
| 4,874,944 A | 10/1989 | Kato | |
| 5,777,324 A | * 7/1998 | Hillenkamp | 250/288 |
| 5,808,300 A | * 9/1998 | Caprioli | 250/288 |
| 6,071,610 A | * 6/2000 | Jarrell et al. | 428/335 |
| 6,265,715 B1 | * 7/2001 | Perreault et al. | 250/288 |

FOREIGN PATENT DOCUMENTS

| | | |
|---|---|---|
| GB | 2 317 495 A | 3/1998 |
| JP | 63-318061 | 12/1988 |
| JP | 7-209252 | 8/1995 |

OTHER PUBLICATIONS

Mehl, J.T., et al., "Coupling Protocol for Thin Layer Chromatography/Matrix–assisted Laser Desorption Ionization", Chromatographia, Oct., 1997, pp. 358–364, vol. 46, No. 7/8, Oct. 1997, Vanderbilt University, Nashville, Tennessee, US.

* cited by examiner

*Primary Examiner*—Jack Berman
*Assistant Examiner*—Kalimah Fernandez

(57) ABSTRACT

The invention relates to the coupling of thin-layer chromatography with mass spectrometry with ionization of the separated analyte substances by matrix-assisted laser desorption (MALDI).

The invention performs thin-layer chromatography (TLC) directly on a contactable, electrically conductive carrier plate which, after generation of small matrix crystals at the surface by suitable application of a matrix solution and drying, can be directly inserted into a mass spectrometer so that the chromatographically separated analyte substances contained in the matrix crystals, can be ionized and analyzed by MALDI mass spectrometry. The invention covers type and shape of the carrier plates and the application procedure of the matrix solution to the carrier plates for MALDI analysis.

18 Claims, 2 Drawing Sheets

TLC/MALDI CARRIER PLATE AND METHOD FOR USING SAME

The invention relates to the coupling of thin-layer chromatography with mass spectrometry with ionization of the separated analyte substances by matrix-assisted laser desorption (MALDI).

The invention performs thin-layer chromatography (TLC) directly on a contactable, electrically conductive carrier plate which, after generation of small matrix crystals at the surface by suitable application of a matrix solution and drying, can be directly inserted into a mass spectrometer so that the chromatographically separated analyte substances contained in the matrix crystals, can be ionized and analyzed by MALDI mass spectrometry. The invention covers type and shape of the carrier plates and the application procedure of the matrix solution to the carrier plates for MALDI analysis.

PRIOR ART

While gas chromatography (GC) and liquid chromatography (HPLC) have been routinely coupled to mass spectrometers with substantial success for some time now and instruments for these "hyphenated techniques" (GC/MS, LC/MS) are commercially available from a number of vendors, that is not the case with thin-layer chromatography (TLC).

Thin-layer chromatography is used for many analytical tasks as a fast, simple procedure for performing quality inspections, determining reaction rates, progress of syntheses, separation of rare earth metals, doping tests in sport, in clinical chemistry and diagnostics, for narcotic tests in criminal proceedings, in forensic chemistry, residue analyses for pesticides, and many other fields. It is performed very. much like liquid chromatography with a liquid and a solid phase, whereby the migration of the liquid phase is solely caused by the capillary effect of the open-pore solid phase which is applied to a solid carrier plate in form of a thin layer. The procedure is simple and inexpensive. As with liquid chromatography, there are two types of thin layer chromatography: adsorption chromatography and distribution chromatography.

Knowledge of thin-layer chromatography is assumed here. Small volumes of various solutions containing the substance mixtures to be separated are applied as spots to the porous thin layer on a starting line. The edge of the carrier plates below the starting line is then immersed in a liquid mobile phase in a closed vessel at saturated vapor pressure for the liquid mobile phase, whereby the capillary migration of the mobile phase in the porous thin layer takes the individual substances with it. With different adsorption or distribution coefficients the analyte substances are transported at different rates and are thus separated. After removing and drying the carrier plates the analyte substances are distributed over the plate as spots along invisible tracks, which begin at the starting point of the mixtures and follow the front of the solvent. In this way ten to thirty mixtures can be separated on a single carrier plate simultaneously in parallel tracks.

For highly complex mixtures, two-dimensional thin-layer chromatography is also known. It consists of separating a mixture sample close to the edge in one direction at first. After drying the thin layer on the carrier plate a second separation of the substances, which have already been separated in one dimension, can be performed with a second mobile phase with different distribution coefficients, perpendicular to the first track.

Unless in the relatively rare case of colored substances, the substances distributed as spots cannot be seen with the naked eye. If the substances fluoresce, it is possible to see and measure the substances by exciting their fluorescence. In other cases the substances have to be stained after drying the plates. A fluorescing background can also be used for detection because the substances can be recognized by attenuation of fluorescence. However, under no circumstances –as in all chromatographic methods with merely intensity-indicating detectors - can unambiguous identification of the substances be performed with these methods of detection. Although there are indeed methods with high separation efficiency due to the development of perfectly uniform thin layers (so-called HPTLC=high performance thin layer chromatography), detection remains the weak point of thin-layer chromatography.

If one disregards the analysis of individual, usually scraped spots of substance by mass spectrometry, only relatively few extensive attempts have been made with mass spectrometric analysis of the substances separated by thin-layer chromatography. Probably the best and most recent work in this area is from J. T. Mehl, A. I. Gusev and D. M. Hercules "Coupling Protocol for Thin Layer Chromatography/Matrix-assisted Laser Desorption Ionization" Chromatographia 46, 358 (1997). The authors report on various methods of mass spectrometric analysis in time-of-flight spectrometers, including their own experiments on direct MALDI ionization from the TLC plate, for which they report weak sensitivity, bad resolution, and rather bad mass resolving power. For this reason they developed an elaborate "second generation" of coupling TLC/MS in order to avoid these disadvantages, and this consists of transferring the analyte substances from moistened TLC plate onto a MALDI sample support plate provided with a matrix, without any chromatographic thin layer. This more complicated method is presented by the authors as a much more satisfactory solution to the problem.

The inferior resolution of the former method must be due, in a manner as yet unexplained, to a lateral transport of the analyte substances during MALDI preparation. The inferior mass resolving power may have various causes, which can range from a charging of the thin layer to inferior definition of the ion-accelerating electric field by the base of the thin-layer plate.

OBJECTIVE OF THE INVENTION

Methods and devices should be found for simple and rapid qualitative or quantitative mass spectrometric analysis of analyte substances separated by thin-layer chromatography, with potential for automization and high sample throughput.

SHORT SUMMARY OF THE INVENTION

It is the basis of the invention to perform thin-layer chromatography directly on specially prepared and designed mass spectrometry sample support plates which are electrically conductive under the chromatographic thin layer and accessible to good electrical contact, and to extract the locally separated analyte substances from the porous chromatographic thin layer to the surface without any major lateral transport and generate a surface layer of matrix crystals containing the analyte substances on top of the porous chromatographic thin layer, introducing the carrier plates into the mass spectrometer, and qualitatively or quantitatively analyzing the analyte substances after ionization with matrix-assisted laser desorption (MALDI) by mass spectrometry directly from the thin-layer carrier plate.

By contrast with the description in the above-cited article, scans of the analyte substances can be obtained with a high level of sensitivity and reproducible concentration determination, with good substance separation and high mass resolving power. It seems to be crucial to bring the carrier plates in the mass spectrometer electrically up to acceleration potential without any major contact resistances. Furthermore, certain additional conditions in the extraction process for the analyte substances by the matrix solution have to be strictly maintained. The scans are surprisingly clean: generally they only contain the analyte ions and the ions of the matrix substance.

For determination by mass spectrometry it is possible to use both time-of-flight mass spectrometers and the various types of ion trap mass spectrometer (RF ion trap spectrometers or ion cyclotron resonance mass spectrometers).

Qualitative analysis, which means the identification of the substances, may be performed using libraries which contain both the masses and the mobile phase and layer specific $R_f$ values of the substances ($R_f$=quotient of the migration rate of the substance and the migration rate of the mobile phase in the thin layer).

To improve identification of unknown substances, fragment ion spectra can be generated, for instance daughter ion spectra in ion trap spectrometers or the well-known PSD spectra in time-of-flight mass spectrometers (PSD=post source decay). These fragment spectra from MALDI ions are similar (with limitations) to the spectra which are obtained from the same substances by means of electron impact; for electron impact there are spectrum libraries containing hundreds of thousands of spectra. Studies of the differences in the fragmentation of protonated substances by contrast with electron impact fragmentation are being conducted at present.

Transport of the analyte substances from the bulk of the porous chromatographic layer into the surface layer of small matrix crystals, formed during the process, is critical. An adequately but not oversaturated soaking of the porous layer with a matrix solution followed by immediate drying is necessary for this. The drying process draws the matrix solution to the surface by capillary action, whereby the substances are entrained by being dissolved in accordance with their coefficient of distribution between porous layer and matrix solution. High solubility in the matrix solution helps to extract a large fraction each of the various substances. The entrainment displays surprisingly good quantitative reproducibility. The analyte substances are integrated into the scarcely visible matrix crystals forming at the surface or imbedded in grain boundaries. Lateral migration of the matrix solution in the thin layer can be avoided by the methods given below so that there is no measurable loss of lateral resolution of the thin-layer chromatogram or adulteration of the $R_f$ values.

For soaking the porous layer with the matrix solution, printing has proved successful, for example with an elastic printing roller covered with the correct amount of solution or with an appropriate printing plate, as has spraying on a very fine mist of droplets. For the printing procedure, a printing plate can, for example, be used which is covered with a fine-pore foam rubber, whereby the foam rubber contains the matrix solution but is almost dry. Only when the printing plate is pressed on with relatively strong pressure is matrix solution given off to the highly absorbent thin layer, soaking the thin layer completely, and if the printing plate is lifted off carefully the excess of matrix solution is immediately also lifted off by the fine-pore foam rubber so that there can be no lateral migration. Printing is also best performed automatically in order to obtain a homogeneous printing layer of matrix solution.

For spraying it has been found that first the spraying procedure has to be completed within as short a time as possible, that second the droplets of the matrix solution have to be very small (approximately between one picoliter and one nanoliter in volume), but they must not dry out on their journey between the tip of the spray capillary and the carrier plate, and that third the density and duration of the mist of droplets must be such that continuous, saturated moisturizing or soaking of the porous thin-layer chromatography layer is achieved without any excess liquid. Spraying is therefore best performed automatically, whereby the matrix solution is best sprayed from below toward the carrier plate mounted on a carriage, which can be moved in two directions above the spray capillary.

The TLC/MALDI carrier plates used for the method should preferably be the same size as microtiter plates having useful surface areas of 78×108 millimeters because they can then be easily stacked and be picked up and processed by modern pipetting robots with their grab arms, and thus can also be transferred to the mass spectrometer. Specially designed carrier plates can also be mounted on frames so that the carrier plate and frame together produce the outer shape of a microtiter plate. Modern mass spectrometers process sample support plates the size of microtiter plates, whereby two-dimensional precision sensing of the surface is possible. The TLC/MALDI plates can be provided with a continuous thin layer, but also with individual thin-layer tracks, whereby it is favorable to provide the strips between the tracks with a hydrophobic surface.

Figure 1:
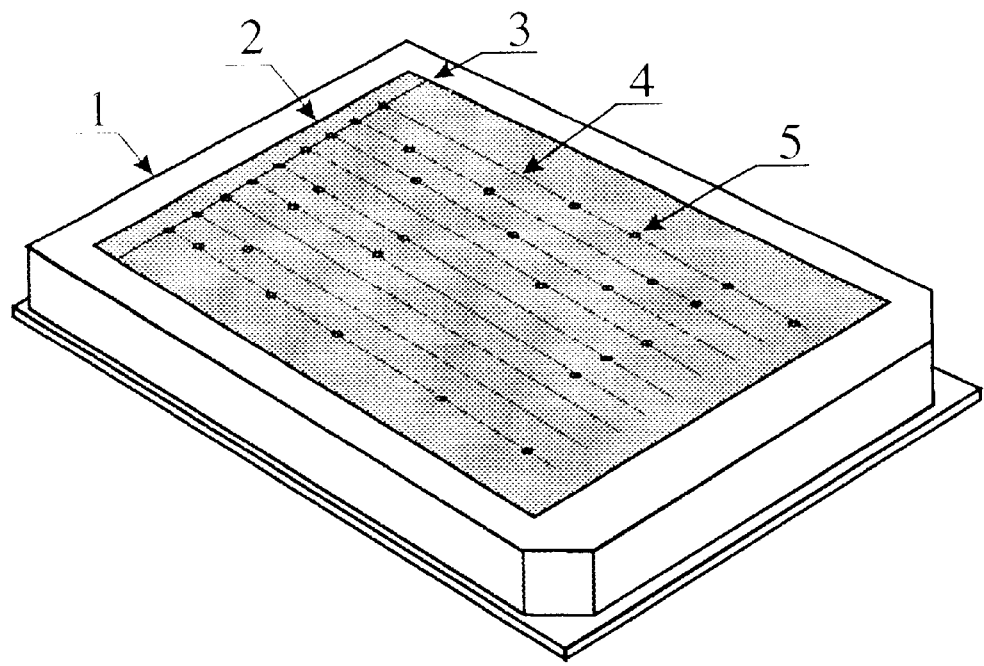
FIG. 1 shows a metallic thin-layer carrier plate (1) in the shape of a microtiter plate, with a rectangular chromatographic thin layer area (2) on top. At the starting line (3) there are residues of the applied analyte substance mixture and the (in principle invisible) separated analyte substances are visibly drawn as analyte substance spots (5) along the invisible tracks (4, drawn as broken lines). Contact with the metal plate can be made around the thin layer area (2).
Figure 2:
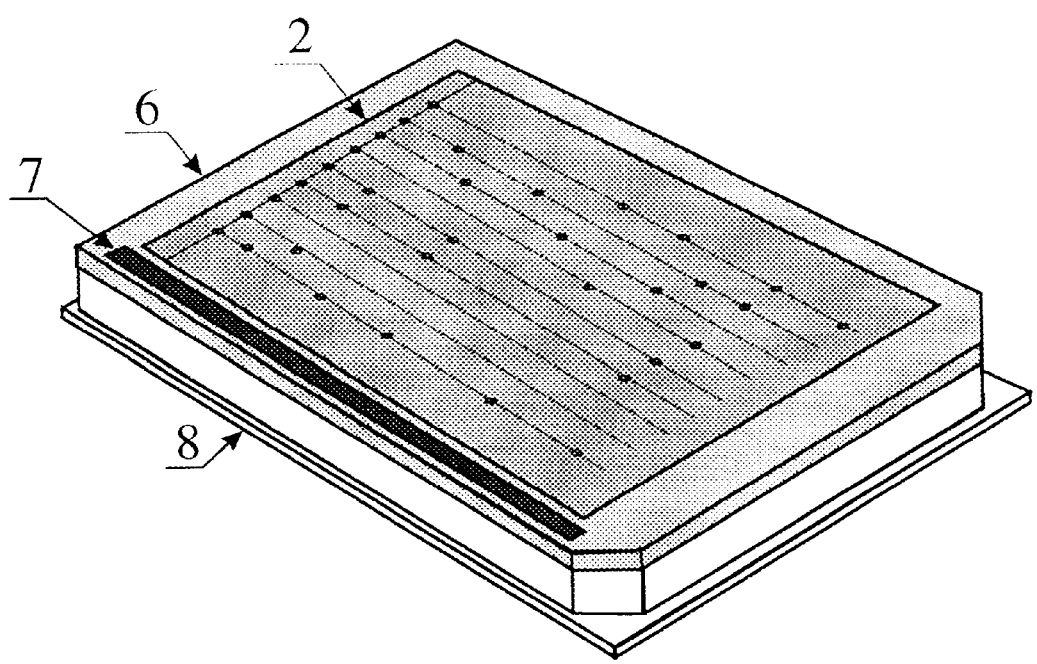
FIG. 2 shows a thin-layer carrier plate (6) made of glass, which bears a conductive layer under the porous chromatographic thin layer (2), with a specially applied contact strip (7). The carrier plate (6) is mounted on a frame (8), which together with the carrier plate (6) produces the shape of a microtiter plate.
Figure 3:
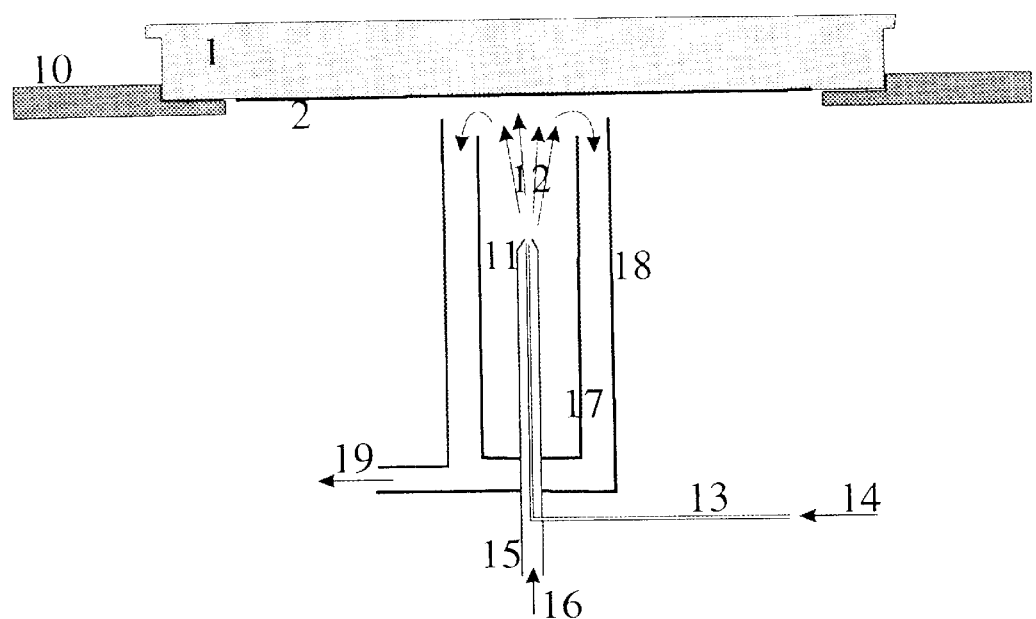
FIG. 3 shows the spraying of a thin layer (2) on a carrier plate (1), which is on the frame (10) of a movement unit not shown here, with a spray mist (12) of tiny droplets of matrix solution.

The mist (12) is made by the tip of a spray needle (11), which is comprised of an inner capillary (13) and an outer capillary (15). The inner capillary (13) feeds the matrix solution (14), while the outer capillary (15) feeds the nebulizer gas (16). The tip of the spray (11) is surrounded by two concentric cylinders (17, 18), between which any excess mist (12) is drawn off in the direction of a pump (19).

PARTICULARLY FAVORABLE EMBODIMENTS

A particularly favorable embodiment of the method is based on carrier plates (1) the size of microtiter plates, which are provided with a TLC thin layer area (2), for instance made of silica gel 60 and titanium oxide, the size being 78×108 millimeters. Microtiter plates with an upper surface of this size have become widespread as an industry standard; all the pipetting robots used in biochemistry can handle plates of this size. Carrier plates of this type can be stacked without the thin layer being touched or damaged. The carrier plates can, for instance, be made of aluminum. The precise shape of the carrier plates (within the tolerances for the standard size of microtiter plates) depends on the holding device of the mass spectrometer.

A modification of carrier plates can consist of plates two or three millimeters thick (6) with the thin layer which only produce the dimensions of the microtiter plate together with a holding frame (8). These thin-layer plates (6) which can be mounted on the holding frames (8) can, for example, be made from glass or ceramics instead of aluminum, whereby they then have to be coated with an electrically conductive layer accessible via a contact surface (7) under the TLC thin layer; the conducting layer defining the acceleration potential of the ions in the mass spectrometer. Mounting the plates on the holding frames can be performed by combination of standardized bolts and nuts, or simply by glueing, for instance with double-sided Scotch tape.

On these plates (either 1 or 6) thin-layer chromatography is performed in the normal way. The substance mixtures are applied in volumes of approx. 1 microliter of solution each to the starting points along the starting line (3), whereby, as usual, a free marginal zone of about 10 millimeters remains on the right and left of the field of samples on the thin layer in order to avoid boundary disturbances. If the selected direction of migration is the longitudinal direction of the carrier plate, there will be a total of 14 tracks (4) each with a length of about 100 millimeters with a spacing of four millimeters between each sample. If the spacing is three millimeters there will be 18 tracks. The length of the tracks, about 100 millimeters, is the same as that of commercially available TLC plates.

After applying the sample mixture solutions the plate is "developed" by placing it upright in the mobile phase with the base below the starting line. The "development" takes place in a vessel which provides a saturated vapor of the mobile phase and avoids disturbances due to drafts. Depending on the mobile phase and the thickness and type of thin layer, development takes between one and sixty minutes. The carrier plate is removed when the mobile phase front has almost or completely reached the upper edge by capillary migration. The thin layer is then carefully but quickly dried in dust-free air or an inert gas at approx. 60 to 80 degrees Celsius.

The substances (5) are now distributed as spots along invisible linear tracks (4) which extend from the respective starting point on the starting line (3) to the last mobile phase front. The spots (5) have diameters of around 1 millimeter.

To make them ionizable by MALDI, the analyte substances (5) should preferably be imbedded in a layer of matrix crystals. This layer should be at the surface of the plate (1, 6). In principle this is performed by moistening the thin layer (2) to saturation with a matrix solution and then drying it.

The matrix solution, e.g α-cyanohydroxycinnamic acid in a mixture of methanol and water, or also dihydroxybenzoic acid in water, can be simply printed on with a moist roller coated with a thin layer of foam rubber, rolling quickly. Care must be taken to ensure that no migrating solution pile-up develops in front of the effluent surface of the roller; on the other hand however, the thin layer must be moistened to saturation. The complete moistening to saturation is crucial, but no excess matrix solution should be left at the surface; so the excess matrix solution must be removed by the foam rubber layer immediately. Maintenance of the correct roller moisture for a lengthy period of time without complete washing, drying and reloading poses some difficulties but the printing is useful if there is a large quantity of work, i.e. if sample throughput is high. Instead of the roller, printing plates can also be applied, as described above, which can be used more simply for manual application of the matrix solution.

Spraying on a mist of droplets (12) from the matrix solution is relatively easy to monitor. Here too care must be exercised. The droplets must reach the surface of the thin layer (2) in an undried state, i.e. still liquid, and the thin layer must just be soaked to saturation until the surface begins to shine, but without creating any visible excess of solution on the surface. The spray strips must be evenly laid out adjacent to one another in order to achieve homogenous moistening of the thin layer without any lateral migration of the solution. The next spray strip must be applied within as short a time as possible in order to prevent capillary migration for more than one second also at the margin between the last spray strip and the dry thin layer.

The size of the droplets is particularly important. The droplets must have a diameter of approximately 10 to 50 micrometers. Larger droplets, as are made by fixation sprays or perfume atomizers, are not suitable because they immediately cause lateral migration in the thin layer away from the point where the droplets are applied and therefore diminish the resolution of substance separation. A concentric arrangement (11) of two thin capillaries (13, 15), as also used for electrospray methods, has proved successful as a nebulizer. Both the admission of air or nitrogen (16) through the outer capillary (15), and the transport of the matrix solution (14) through the inner capillary (13) must be controlled efficiently, for example by a spray pump in the case of the matrix solution.

Electrospray, on the other hand, has not proved successful because the enrichment or depletion of the droplets with protons by the electrospray process creates extremely acid or extremely alkaline droplets which can change sensitive substances chemically. Also, electrolytic processes take place in the thin layer and these can decompose the substances.

When drying the thin layer, the matrix solution with the dissolved analyte substances is drawn to the surface by capillary action due to the progressing evaporation of the liquid at the surface; here the matrix substance starts to form microscopically small crystals on top of the chromatographic thin layer. The crystals grow slowly and enclose thereby single analyte substance molecules, separated from each other, ideally for MALDI. After drying, the still tiny matrix crystals are hardly visible at the surface. However, they are ideally placed and suited for the MALDI process.

The reproducibly saturated moistening of the thin layer with matrix solution of a predetermined concentration and the ensuing drying process with transport of the analyte substances to the surface and its growth of superfine matrix crystals is crucial to a quantitative evaluation of the spectra.

After drying, the carrier plate (1, 6), if necessary mounted on its frame (8), is introduced into the ion source of a mass spectrometer through a vacuum lock. Via a contact surface (7) on the conductive base next to the thin layer, the carrier plates are brought up to the required electrical potential, which, for instance, is about 30 kilovolts in time-of-flight spectrometers. In the case of plates made from alumin special measures are necessary to enable reliable contact, for example by nickel-plating or gold-plating a contact surface. In the case of carrier plates made from glass or ceramics conductive layers are necessary under the thin layer, and here too, good contact must be guaranteed.

The ion source is provided with an x-y moving station which can move the carrier plate very precisely and reproducibly in the longitudinal and transverse directions. The point to be analyzed is moved to the focal spot of a pulse laser, whereupon the laser beam is pulsed and a small quantity of matrix substance including the analyte molecules is vaporized in the vacuum. The focus of the laser is usually set to a diameter of 100 to 200 micrometers. In the vaporization cloud some of the matrix molecules will be ionized due to the high vaporization temperature; some of these matrix ions will proceed to collide with analyte molecules and ionize them by giving off protons. The high vaporization temperature is diminished within an extremely short time period by the adiabatic expansion process of the cloud into the ambient vacuum. In a time-of-flight mass spectrometer, which here serves as an example, the ions are then accelerated by the voltages applied in the ion source and shot into a flight section. From the arrival time at a detector their velocity and thus their mass can be calculated.

Usually about 5 to 50 individual spectra are acquired by a sequence of laser pulses. They are added together to produce a sum spectrum which has a better signal-to-noise ratio than the individual spectra. To obtain the individual spectra for a sum spectrum it is sometimes useful to move the carrier plate slightly from spectrum to spectrum.

The MALDI spectra are generally very simple because there are practically no multiply charged ions and no fragment ions. This spectrum therefore usually only contains the singly charged molecular ions of the analyte substance, and the known ions of the matrix substance.

From the spectrum it is thus possible to calculate the molecular mass m of the analyte substance and its $R_f$ from its known place on the carrier plate; mass m and $R_f$ determine the analyte substance. The quantity of analyte substance can –after calibration –be determined from the signal intensity.

If the tracks (4) are fairly straight, about twenty individual spectra per spot are necessary for a sum spectrum. If about 4 sum spectra per millimeter of track are to be scanned, the substances on the 14 tracks can be automatically measured in about two hours with a high resolution, if 20 laser shots can be fired per second and the carrier plate can be moved fast (0.25 millimeters in about 0.2 seconds). An initial identification and quantification can be performed with a data system in real time. If carrier plate feed is automatic, analyses of 168 mixtures on 12 carrier plates can in this way be handled automatically in 24 hours.

If, on the other hand, it is only individual parts of the mixture which are of interest, for example only a single analyte substance per track which can be defined with an accuracy of plus/minus one millimeter on its track, the 14 individual analyses of a carrier plate can be performed in about three minutes. Then the introduction times of the carrier plate, which are about five minutes, become the factor which determines time. If the carrier plates are fed automatically, over 2,000 individual analyses can be performed on over 150 carrier plates per day.

This type of analysis assumes that the analyte substance can be determined from the mass m and the coefficient $R_f$ with sufficient clarity. Usually a laboratory soon has sufficient data to permit such work. However, if one encounters an unfamiliar substance, the acquisition of a daughter ion spectrum is advisable.

Daughter ion spectra can be measured both in time-of-flight spectrometers and in ion trap spectrometers. In time-of-flight spectrometers both PSD and ISD spectra can be measured (PSD=post source decay; ISD=in source decay). With PSD the ions which have become metastable in the laser ablation cloud, decompose after their acceleration in the drift flight section. Due to their different masses and therefore different depths of penetration into the reflector, the fragment ions of the metastable decomposition can be measured after reflection. By contrast, if one increases the energy of the laser for ISD, the ions decompose practically spontaneously in the ion source. Fragment ions can therefore already be measured using their differing flight velocities after the same acceleration in the linear mode of the spectrometer. In ion trap mass spectrometers the fragment ions are generated in the known manner by collisions in the ion trap cell itself.

The composition of fragment ions in the daughter ion spectra is similar to that in the spectra which are obtained for the same substance by electron impact, although the intensities of the fragment ions relative to one another are often very different. For electron impact spectra there are spectrum libraries available with hundreds of thousands of spectra. Many search algorithms for these libraries are written so that they only take into account the relative intensities to a very minor extent because the electron impact spectra of various instruments already manifest considerable differences in intensity. These search programs can therefore also be used for the substance search based on MALDI fragment ion spectra.

For applying the matrix solution onto the porous thin layer it is preferable to use an automatic spray with a movement device. The spraying is made possible by a concentric arrangement (11) of two capillaries (13, 15), of which the inner capillary (13) feeds the matrix solution (14) and the outer capillary (15) feeds the spray air (16) or the spray nitrogen. Such spray tips (11) are known from gas-assisted electrospraying. A precise migration of matrix solution (14) can be achieved with a spray pump. To prevent any inadvertent dropping of the matrix solution onto the thin layer, the spray tip should preferably be pointed up and the thin-layer plate (1) is guided by the movement device over the spray jet (12). The spray zone near the thin layer can also be provided with a concentric suction device comprising two cylinders (17, 18) for the excess spray mist in order to obtain a defined limitation of the spray strips. The spray strip is about 10 to 15 millimeters wide for a spray tip spacing of about 20 millimeters. With automation it is possible to achieve a very homogeneous application in a defined short time.

The carrier plate with contiguous thin layer can also be used for two-dimensional thin-layer chromatography. Scanning the entire surface in the mass spectrometer takes a long time though: even if scanning only takes place at a resolution of 0.5 millimeters, the scanning of a surface 70×100 millimeters may take about 9 hours. It is therefore useful to introduce limitations in area, whereby the usual standard detection methods may already be of assistance in working out these limitations.

For high analysis throughput the tracks can also be closer. Particularly a coating of the carrier plate with separated thin layers can be created for the individual tracks. If track width is one millimeter and there is 0.5 millimeter empty strips in between it is easy to achieve over 40 tracks each with a length of 100 millimeters on a carrier plate the size of a microtiter plate. Avoidance of boundary effects on each track, however, calls for special measures in selecting the layer materials and preparing the base. It is particularly favorable if the strips between the tracks are hydrophobic because then there will be no residues of the dried matrix solution. These will be completely absorbed by the thin-layer tracks.

What is claimed is:

1. Method for mass spectrometric analysis of analyte substances separated by thin-layer chromatography with ionization of the analyte molecules by matrix-assisted laser desorption (MALDI), comprising the following steps:

(a) providing a thin-layer chromatographic carrier plate either made from metal or with a electrically conductive layer under the chromatographic thin layer, with a contact area for the electrically conductive surface under the chromatographic layer, (b) separating the analyte substances by thin-layer chromatography on the carrier plate, (c) drying the thin-layer chromatographic carrier plate, (d) evenly soaking the chromatographic thin layer with matrix solution, (e) fast drying of the chromatographic thin layer, whereby the substance molecules are at least partially transported to the layer surface by the capillary stream of matrix solution generated by the superficial evaporation and are enclosed in tiny matrix substance crystals formed by the drying process, (f) introducing the thin-layer chromatographic carrier plate into the ion source of a mass spectrometer, (g) contacting the electrically conductive layer under the chromatographic thin layer with the acceleration potential for the ions to be formed, and (h) analyzing the substances by matrix-assisted laser desorption and ionization (MALDI) mass spectrometry.

2. Method according to claim 1, wherein the soaking of the chromatographic thin layer with matrix solution is performed by printing with an elastic printing roller or printing plate.

3. Method according to claim 2, wherein the printing roller or printing plate is coated with a thin layer of foam rubber which contains the matrix solution.

4. Method according to claim 1, wherein the soaking of the chromatographic thin layer with a matrix solution is performed by a fine mist of droplets generated by spraying the matrix solution.

5. Method according to claim 4, wherein the mist consists of droplets with diameters of between 5 and 50 micrometers.

6. Method according to claim 4, wherein the carrier plate is moved through the spray mist by an automatic movement device above a vertical spray tip.

7. Method according to claim 1, wherein a daughter ion spectrum is acquired for more accurate identification of a substance.

8. Method according to claim 1, wherein a time-of-flight mass spectrometer, an RF ion trap mass spectrometer or an ion cyclotron resonance mass spectrometer is used to determine the substances.

9. Thin-layer chromatography plate for performing the method of claim 1, wherein the plate has a size which corresponds to the outer contours of a microtiter plate, either by its own or together with a holding frame, holds a chromatographic thin layer on its surface, is electrically conductive under the chromatographic thin layer, and has electric contact areas.

10. Thin-layer chromatography plate according to claim 9, wherein the plate holds the chromatographic thin layer in an area of about 78×108 millimeters in size.

11. Thin-layer chromatography plate according to claim 9, wherein the plate under the chromatographic thin layer has a conductive layer, which is contactable at the margin outside of the chromatographic thin layer.

12. Thin-layer chromatography plate according to claim 9, wherein the plate has individual thin-layer tracks transversely or longitudinally.

13. Thin-layer chromatography plate according to claim 12, wherein the strips between the tracks are hydrophobic.

14. Method for mass spectrometric analysis of analyte substances, the method comprising:

separating the analyte substances by thin-layer chromatography wherein the chromatographic thin-layer is located on a carrier plate having an electrically conductive layer;

drying the chromatographic thin layer;

soaking the chromatographic thin layer with matrix solution;

drying the chromatographic thin layer so that analyte substance molecules are at least partially transported to the layer surface by a capillary stream of matrix solution and are enclosed in tiny matrix substance crystals formed by the drying process;

introducing the carrier plate with the matrix substance crystals into a mass spectrometer; and analyzing the substances by matrix-assisted laser desorption and ionization.

15. A method according to claim 14, wherein the electrically conductive layer of the carrier plate is provided with an acceleration potential for the ions to be formed during ionization.

16. Thin-layer chromatography plate for analyzing substances using thin-layer chromatography and MALDI mass spectrometry, the plate comprising:

at least one chromatographic thin-layer on the plate that allows the performing of a chromatographic separation on the plate surface;

an electrically conductive layer under the chromatographic thin layer to which an electrical acceleration potential may be connected; and a profile that allows the plate, either alone or together with a holding frame, to be mounted in the ionization chamber of a MALDI mass spectrometer.

17. Thin-layer chromatography plate according to claim 16, wherein the plate comprises a plurality of thin-layer chromatography tracks.

18. Thin-layer chromatography plate according to claim 17, further comprising hydrophobic regions between adjacent chromatography tracks.

* * * * *